United States Patent [19]

Weitzman et al.

[11] 4,267,167

[45] May 12, 1981

[54] THIXOTROPIC TOPICAL FLUORIDE-PHOSPHATE GEL COMPOSITIONS USEFUL FOR THE PREVENTION OF DENTAL CARIES

[75] Inventors: Stewart Weitzman, Portland; Roy D. Archibald, Gresham, both of Oreg.

[73] Assignee: Cooper Care, Inc., Palo Alto, Calif.

[21] Appl. No.: 153,089

[22] Filed: May 27, 1980

Related U.S. Application Data

[63] Continuation of Ser. No. 626,068, Oct. 28, 1975, abandoned.

[51] Int. Cl.³ .................. A61K 7/18; A61K 33/16; A61K 33/42
[52] U.S. Cl. ........................ 424/52; 424/57; 424/128; 424/151
[58] Field of Search .............. 424/52, 57, 128, 151; 252/316, 317

[56] References Cited

U.S. PATENT DOCUMENTS

| | | | |
|---|---|---|---|
| 2,678,902 | 5/1954 | Mehaffey | 424/357 |
| 3,337,412 | 8/1967 | Elbreder | 424/128 |

OTHER PUBLICATIONS

Veegum (1964) R. T. Vanderbilt Co., Inc., N.Y., N.Y. Bulletin No. 44, 33 pp.
Laughner Am. Perf. & Cosm. 81(10); 51–52, Oct. 1966 Functions of Fumed Silica in Cosmetic-Drug Products.
Aerosil (1970) Degussa Bull. No. 49, Aerosil in Pharmaceuticals and Cosmetics.
Ferch (1970), Chem. Abstract 73#18448 U Aerosil Properties with Regard to its Use for Cosmetics.
"Cabosil" Properties and Functions Cabot Corp., 36 pp.

*Primary Examiner*—Shep K. Rose
*Attorney, Agent, or Firm*—Chernoff & Vilhauer

[57] ABSTRACT

A thixotropic acidulated phosphate fluoride composition for the control and prevention of dental caries is disclosed.

6 Claims, No Drawings

THIXOTROPIC TOPICAL FLUORIDE-PHOSPHATE GEL COMPOSITIONS USEFUL FOR THE PREVENTION OF DENTAL CARIES

CROSS-REFERENCE TO RELATED APPLICATION

This is a continuation of application Ser. No. 626,068, filed Oct. 28, 1975, now abandoned.

BACKGROUND OF THE INVENTION

This invention relates to improvements in fluoride-phosphate compositions for topical application to the teeth for the control and prevention of dental caries. More particularly, the present invention is directed to an improved thixotropic solution having gel-like handling characteristics which has acid and heat stability, and other desirable properties for use in the formulation of a gel-like topical fluoride-phosphate dental composition. The thixotropic agents disclosed herein are solutions rather than true gels, but when immobilized for a short period of time they set up and assume a gel-like appearance which, however, is fully reversible as the composition can readily be returned to a fluid state by simple agitation. For convenience of reference, and because of the similarities in certain particulars, specifically their end application, the therapeutic dental fluoride gel-like compositions of the present invention will be referred to hereinafter in abbreviated form as fluoride "gels."

In Elbreder U.S. Pat. No. 3,337,412 there is disclosed various topical fluoride-phosphate gel compositions useful in the control and prevention of dental caries which are comprised of a fluoride component, an acid phosphate component and a gelling agent. The gelling agents disclosed by Elbreder as being useful in the composition of such fluoride gels, include those of the cellulose type, e.g. hydroxyethyl cellulose and carboxymethyl cellulose, and silica-based gelling agents such as magnesium aluminum silicate and silica aerogel. The gelling agents indicated by Elbreder as being suitable are those which possess the characteristics of being substantially acid-stable in a pH range of approximately 1.8 to 4.5, compatible with fluoride under such acid conditions, and impart a viscosity to the resultant fluoride gel composition of between approximately 7000 and 100,000 centipoises.

While fluoride gel compositions of the type disclosed by Elbreder have been widely adopted for use in the treatment and control of dental caries, it has been found that there are certain practical and clinical disadvantages present in the Elbreder-type product resulting from inherent deficiencies in the gelling agent selected. Specifically, because of the relatively high viscosity of the Elbreder-type cellulose and silica-based gelling agents, it is difficult for the user to conveniently, uniformly and completely dispense the product from the packaging container onto the individual applicator tray prior to its insertion into the mouth of the patient. The same high viscosity characteristic of the gelling agent, which enables the fluoride gel composition to adhere well to the teeth and applicator tray and not thin out in the presence of saliva and run down into the throat, operates against the composition's having sufficient flowability to adequately penetrate and protect the interproximal surfaces of the teeth. Further, it has been found that cellulose and silica-type gelling agents of the type disclosed by Elbreder tend to be unstable in the presence of the highly acid environment of the fluoride-phosphate gel composition and tend to thin out with the passage of time if not refrigerated, thus reducing the useful shelf life of the product.

The present invention is directed to an improved agent for use in the formulation of topical dental fluoride compositions which substitutes, for the cellulose and silica-type gels disclosed by Elbreder, a gel-like solution having thixotropic properties. By simple agitation of the thixotropic composition, such as by manually shaking the bottle or other bulk container in which it is stored, the viscosity of the composition is greatly reduced so that the material becomes readily flowable and liquid-like, thus enabling it to be readily and uniformly dispensed by the user into individual applicator trays. From a preparation standpoint the thixotropic properties imparted to the fluoride "gel" by the composition of the present invention permit the speedy dispensing of the material into bulk containers and later into individual applicator trays, as a liquid-like material is being dealt with in the filling and dispensing procedure rather than a highly viscous gel. This greatly facilitates the feasibility of factory prepackaging of the composition in single-use individual applicator trays which are filled with "gel" and then sealed with a removable lid prior to shipment to the customer. Alternatively, the "gel" because of its thixotropic property can be conveniently dispensed as needed into individual trays from a bulk container at the dentist's office.

Once dispensed into the applicator tray, either in the factory or at the dentist's office, as the thixotropic material is allowed to remain at rest it sets up in a very short time span, on the order of a few seconds, into a highly viscous gel-like material so that, when the tray is inserted into the oral cavity, even in an inverted position against the teeth of the lower jaw, the fluoride "gel" composition remains in the tray, adhering to the teeth and exhibiting unexpectedly far superior capability to penetrate to the interproximal surfaces of teeth not reached by conventional aciduated phosphate fluoride gels as exemplified by the composition disclosed in Elbreder U.S. Pat. No. 3,337,412.

It has further been found that the composition of the present invention does not tend to thin out, drip or run down into the mouth and throat. This non-drip, non-run property is a very important characteristic for a topical fluoride dental composition as it has been found that ingestion of the composition by patients in many cases causes retching, regurgitation and peristaltic cramps. In addition, the improved dental fluoride gel-like composition disclosed herein is highly heat and acid stable for substantial periods of time, thus materially lengthening its shelf life. Further, the thixotropic composition of the present invention has been found, from empirical subjective observations, to greatly enhance the flavor characteristics of the flavoring agent typically employed in fluoride gels to mask out the bitter taste of the acid constituent of the composition. This flavor-enhancement property permits a material reduction in the amount of flavoring agent required to achieve equivalent flavor masking effects.

The present invention employs as a preferred thixotropic agent, in the formulation of topical fluoride-phosphate "gel" compositions of the type described, a complex colloidal magnesium aluminum silicate gum, either alone or in mixtures with relatively small amounts of thickening and/or stabilizing agents. In a preferred embodiment the thixotropic agent, comprised of the mixture of complex colloidal magnesium aluminum silicate and a fumed silica dioxide powder in a ten to one ratio, comprises only about eleven percent by weight of the resultant fluoride "gel" composition. Because of the apparent high viscosity imparted to the resultant composition by the thixotropic gum constituent, it has been found that a lesser quantity of this agent need be employed to obtain the desired degree of set up of the "gel" in the mouth, as compared to the conventional, non-thixotropic gelling agents disclosed by Elbreder. Surprisingly, at the same time, the thixotropic composition of the present invention allows greater penetration of the composition to the interproximal surfaces of teeth than the non-thixotropic compositions disclosed by Elbreder. One gum found especially suitable as the thixotropic constituent for the "gel" mixture herein disclosed is the complex colloidal magnesium aluminum silicate product which is marketed under the trade designation "VEEGUM" by R. T. Vanderbilt Company, Inc., of New York, N.Y. Among the cellulose gums found suitable for use as thickening agents in the mixture are carboxymethyl cellulose and hydroxyethyl cellulose, one suitable form of the latter being that marketed under the trade designation "METHOCEL" by Dow Chemical Company, of Midland, Mich. However, cellulose gum thickeners have been found to be not altogether satisfactory in certain formulations and applications as the low pH of the resultant fluoride "gel" composition, on the order of 3.0 to 5.0, causes the gum to hydrolyze, thus rendering the mixture unstable in time and reducing its effective shelf life. To overcome this problem encountered with cellulose-type thickeners it has been found that better results are obtained by including in the "gelling" mixture, either together with or as a substitute for the cellulose gum, about 1% by weight of fumed silica dioxide micronized particulate which acts as a stabilizer to retain moisture and prevent separation of the "gel" composition in its high acid medium. The silica particulate is also slightly thixotropic in its own right and thus its presence improves this desired property in the resultant "gel" composition. One form of fumed silica dioxide found suitable for this specialized application is a pharmaceutical grade 5, 0.3 micron mesh powder marketed under the trade designation "CABOSIL" by Cabot Corporation, of Boston, Mass.

It has been found that the useful range for the thixotropic constituent of the mixture is 3.5 to 12% by weight of the total fluoride "gel" composition. Below about 3.5% the amount of this constituent is sufficiently small that it does not impart any substantial thixotropic property to the overall composition; on the other hand, amounts of this constituent above the indicated upper range causes the resultant fluoride "gel" composition to become pasty and highly viscous, with a constituency similar to toothpaste, so that the composition does not break up and exhibit the desired fluid characteristics when agitated.

The preferred formulation for the thixotropic fluoride "gel" composition, in accordance with the teachings of the present invention, comprises the following percentage by weight constituents:

| Component | Percentage by Weight |
|---|---|
| Actives: | |
| 1.2% Fluoride Ions | |
| Sodium fluoride USP powder | 2.6 |
| Hydrofluoric acid AR 48% | 0.2 |
| Excipients: | |
| VEEGUM HS complex colloidal magnesium aluminum silicate | 10.0 |
| CABOSIL micronized superfine fumed silica dioxide powder, pharmaceutical grade M5 | 1.0 |
| Phosphoric acid 75%, food grade | 1.3 |
| Sodium saccharin MF (sweetener) | 0.2 |
| Trace amounts of coloring and flavoring agents | — |
| Distilled water | 84.7 |
| | 100.09 |

The thixotropic agent and resulting gel-like material are formulated according to the following procedure:

The VEEGUM and CABOSIL constituents are hydrated is hot distilled water. Sodium fluoride powder is added, together with a solution of coloring agent and sodium saccharin sweetener, and flavoring is then added. The solution is blended well and next the phosphoric and hydrofluoric acids are added with sufficient distilled water to dilute the solution to volume. Then the solution is thoroughly mixed until homogeneous, the pH level checked and, if necessary, sufficient phosphoric acid to adjust the pH to lie within the range of 3.0 to 4.0.

Since, as is generally known, thixotropic compositions exhibit non-Newtonian flow patterns, see for example the pamphlet entitled "VEEGUM," Bulletin No. 32, published by R. T. Vanderbilt Company, Inc., it is not possible to conveniently measure or describe in quantative terms the viscosity characteristics of such compositions, as their viscosity is relative to the method of measurement employed and other measurement variables. Accordingly, it is not meaningful to set forth any specifications as to the viscosity characteristics exhibited by the improved thixotropic fluoride "gel" compositions of the present invention.

The above-formulated fluoride "gel" composition, as previously mentioned, sets up very quickly, on the order of only a few seconds, so that immediately after the composition is dispensed into an applicator tray the tray can be turned upside down and no dripping or running of "gel" can be observed, even after five minutes or longer duration.

When the formulation of the thixotropic or other "gelling" constituents is substantially varied from that set out above it has been found that certain deterioration in desired properties for the "gel" composition result. Specifically, if the percentage of VEEGUM complex colloidal magnesium aluminum silicate is materially reduced from the preferred level of 10%, then the resultant "gel" does not exhibit the desired thixotropic property and does not set up quickly when dispensed for use. On the other hand, as previously mentioned, too much of the thixotropic constituent, above about 12%, produces a pasty, too viscous mixture.

The presence of a stabilizer such as the CABOSIL silica dioxide powder is also important as, when a cellulose gum thickener is used alone, the resulting "gel" is somewhat acid-unstable and will tend to break up and separate in time.

It will be understood that thixotropic components other than the complex colloidal magnesium aluminum silicate referred to herein may be suitably used as the thixotropic component of the fluoride "gel" composition. Also, "gel" thickeners and stabilizers other than the cellulose gums and silica dioxide powder disclosed herein may be suitably used in dental compositions formulated in accordance with the teachings of the present invention.

As various changes could be made in the thixotropic topical fluoride-phosphate "gel" compositions disclosed herein without departing from the scope of the present invention, it is intended that all matter contained in the above description shall be interpreted as illustrative and not in a limiting sense.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only to the claims which follow.

What is claimed is:

1. A fluoride-phosphate dental composition useful for topical application to the teeth for the control of dental caries, comprising a fluoride compound which is soluble in water to provide a source of fluoride ions under acid conditions, an acid phosphate compound which is soluble in water to provide a source of phosphate ions, a thixotropic constituent, and water, said thixotropic constituent serving to impart thixotropic properties to the resulting composition so that it exhibits fluid properties when agitated so as to facilitate its dispensation from a bulk container into a dental applicator tray but, when immobilized, sets up on the tray in a few seconds into a gel-like substance which penetrates to interproximal surfaces of all teeth with which it comes in contact and which, when followed by inversion and insertion of the tray in the mouth cavity over the lower teeth, will not drip, run or thin out in the presence of saliva for a sustained period of time of at least five minutes duration, said thixotropic constituent being compatible with fluoride ions under acid conditions and stable in pH range of approximately 3.0 to 4.5 and being within the range of 3.5 to 12% by weight of said fluoride-phosphate composition.

2. The fluoride-phosphate dental composition of claim 1 wherein said thixotropic constituent is comprised of about 10% by weight of complex colloidal magnesium aluminum silicate.

3. The fluoride-phosphate dental composition of claim 2 wherein said thixotropic constituent further comprises an acid-stabilizing and thickening agent serving to promote longer shelf life and to prevent separation in said composition.

4. The fluoride-phosphate dental composition of claim 3 wherein said stabilizing and thickening agent comprises about 1% by weight silica dioxide powder.

5. The fluoride-phosphate dental composition of claim 1 wherein said thixotropic constituent is comprised of about 10% complex colloidal magnesium aluminum silicate and about 1% silica dioxide powder.

6. The fluoride-phosphate dental composition of claim 1 wherein said dental composition further includes sweetening, coloring and flavoring agents to improve the appearance, taste and acceptability of said composition to patient users.

* * * * *

UNITED STATES PATENT AND TRADEMARK OFFICE
CERTIFICATE OF CORRECTION

PATENT NO. : 4,267,167
DATED : May 12, 1981
INVENTOR(S) : Stewart Weitzman and Roy D. Archibald It is certified that error appears in the above-identified patent and that said Letters Patent are hereby corrected as shown below:

Column 4, line 17     Change "100.09" to -- 100.0 --

Signed and Sealed this

Twenty-seventh Day of October 1981

[SEAL]

Attest:

GERALD J. MOSSINGHOFF

Attesting Officer     Commissioner of Patents and Trademarks